(12) United States Patent
Vértesy et al.

(10) Patent No.: US 6,624,143 B1
(45) Date of Patent: Sep. 23, 2003

(54) CALCIUM SALTS OF LIPOPEPTIDE ANTIBIOTICS, METHOD FOR PRODUCING SAME AND THEIR USE

(75) Inventors: Laszló Vértesy, Eppstein (DE); Werner Aretz, Königstein (DE); Heinrich Decker, Bremtal (DE); Eberhard Ehlers, Hofheim (DE); Michael Kurz, Hofheim (DE); Frank Rainer Schmidt, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/623,022

(22) PCT Filed: Feb. 12, 1999

(86) PCT No.: PCT/EP99/00930

§ 371 (c)(1),
(2), (4) Date: Aug. 25, 2000

(87) PCT Pub. No.: WO99/43700

PCT Pub. Date: Sep. 2, 1999

(30) Foreign Application Priority Data

Feb. 25, 1998 (DE) .......................................... 198 07 972

(51) Int. Cl.$^7$ ............................................. A61K 38/00
(52) U.S. Cl. ...................................................... 514/9
(58) Field of Search ................................ 514/9, 11, 14; 530/317, 323; 435/71, 252

(56) References Cited

U.S. PATENT DOCUMENTS

| | | | | |
|---|---|---|---|---|
| 4,800,162 A | * | 1/1989 | Matson ........................ | 435/135 |
| 5,039,789 A | * | 8/1991 | Fukuda et al. ............... | 530/317 |
| 5,085,990 A | * | 2/1992 | Lancini et al. ............. | 435/252.6 |
| 5,629,288 A | * | 5/1997 | Lattrell et al. .............. | 455/553 |
| 6,291,680 B1 | * | 9/2001 | Ichihara et al. ............. | 548/247 |
| 6,318,023 B1 | * | 11/2001 | Yamashita .................. | 47/57.6 |

FOREIGN PATENT DOCUMENTS

EP 0 629 636 12/1994

OTHER PUBLICATIONS

Berge SM, Bighley LD, Monkhouse DC. Pharmaceutical salts. J Pharm Sci. Jan. 1977;66(1):1–19.*
McMurry. Organic Chemistry, 3rd Edition. Brooks/Cole Publishing Company, 1992.*
Derwent Abstract of EP 0 629 636.

* cited by examiner

Primary Examiner—Karen Cochrane Carlson
Assistant Examiner—Sheridan Snedden
(74) Attorney, Agent, or Firm—Finnegan, Henderson, Farabow, Garrett & Dunner, LLP

(57) ABSTRACT

The invention relates to a calcium salt of the compound of formula (II),

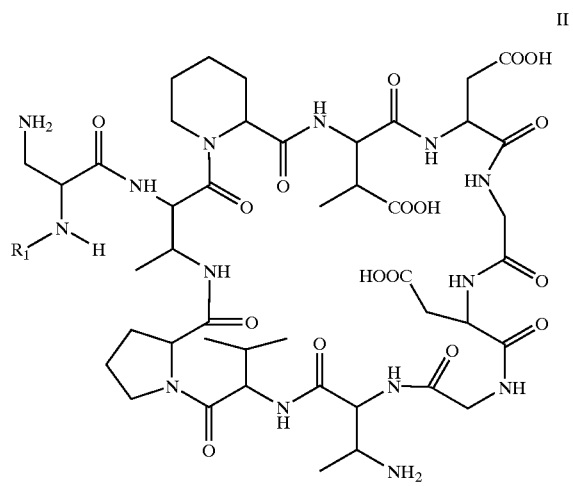

where $R_1$ is a straight-chain or branched, saturated or unsaturated aliphatic acyl radical having 8 to 22 carbon atoms, which can optionally be interrupted by or linked to one or more phenyl or cycloalkyl groups and optionally interrupted by oxygen. The invention also relates to a method for producing said calcium salt and to its use as a medicine.

63 Claims, No Drawings

CALCIUM SALTS OF LIPOPEPTIDE ANTIBIOTICS, METHOD FOR PRODUCING SAME AND THEIR USE

This application is a national stage filing under 35 U.S.C. §371 of international application no. PCT/EP99/00930, filed on Feb. 12, 1999.

The present invention relates to calcium salts of lipopeptide antibiotics, a process for their preparation, and their use.

EP 0 629 636 A1 discloses lipopeptide antibiotics of the formula I

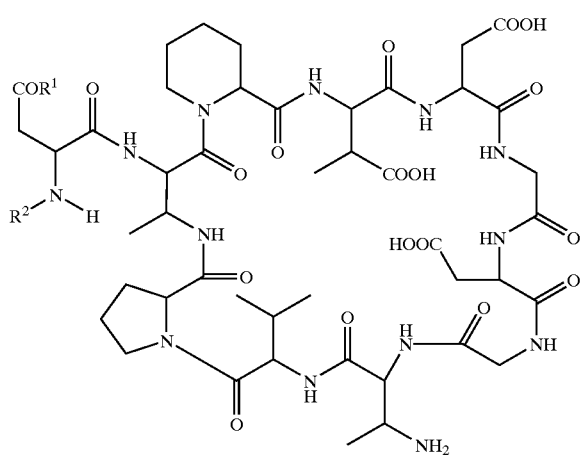

in which $R^1$ is an OH or $NH_2$ group and $R^2$ is a fatty acid radical (R—C(O)—).

These lipopeptide antibiotics can be divided into two groups which differ with respect to their exocyclic amino acid: the lipopeptide antibiotics of the amphomycin type are characterized by the exocyclic amino acid aspartic acid (Asp, where $R^1$ in formula I is an OH group) (R. C. Strong et al., Antimicrobial Agents and Chemotherapy 1970, 42–45; M. Bodanszy et al. J. Am. Chem. Soc. 95, 2352–2357 (1973)), while the lipopeptide antibiotics of the asparagine type are distinguished by the exocyclic amino acid asparagine (Asn, where $R^1$ in formula I is an $NH_2$ group). The lipopeptide antibiotics of the amphomycin type and of the asparagine type differ from each other by substitution on the α-amino group of the exocyclic amino acid (Asp or Asn) having different fatty acid radicals ($R^2$ in formula 1).

Furthermore, EP 0 688 789 A1 (U.S. Pat. No. 5,629,288) discloses derivatives of the lipopeptide antibiotics of the amphomycin type and of the asparagine type and their pharmaceutically tolerable salts. As pharmaceutically tolerable salts of the lipopeptide antibiotics of the formula I, EP 0 688 789 A1 (U.S. Pat. No. 5,629,288) discloses salts with inorganic and organic acids, e.g. hydrochloric acid, sulfuric acid, acetic acid, citric acid, p-toluenesulfonic acid, with inorganic and organic bases such as NaOH, KOH, $Mg(OH)_2$, diethanolamine, ethylenediamine or with amino acids such as arginine, lysine and glutamic acid.

The calcium salt of amphomycin is furthermore known (Kirk-Othmer, Encyclopedia of Chemical Technology, fourth edition, Volume 3, Antibiotics to Batteries, John Wiley & Sons, page 284). It is only sparingly soluble in water and because of the toxicity of amphomycin as a result of its hemolytic activity on systemic use was used exclusively in antibiotic ointments for local application.

The lipopeptide antibiotics of the asparagine type ($R^1$ in formula I is an $NH_2$ group) and their preparation have been described for the first time in EP 0 629 636 A1. The preparation process proposed there, the fermentation of Actinoplanes sp., preferably Actinoplanes friulensis (deposited on Jun. 18, 1990 in accordance with the rules of the Budapest Convention under the Deposit No. DSM 7358 in the Deutschen Sammlung von Mikroorganismen und Zelikulturen GmbH, DSMZ, Mascheroder Weg 1b, D-38124 Brunswick), leads, however, to a mixture of a large number of the structurally closely related lipopeptides of the amphomycin type and of the asparagine type, which have very different properties, in particular different biological actions, such as, for example, their antibacterial action, toxicity as a result of their hemolytic action, and also different physicochemical properties, such as, for example, their solubility and stability, but can only be separated from the culture medium with difficulty. It would therefore be a great advantage to have a fermentation process which essentially leads to the production of preferably only one of the many possible lipopeptide components.

It is an object of the present invention to make available a salt of the lipopeptide antibiotics of the asparagine type which is distinguished by a relatively high stability and good antibacterial activity and can be administered systemically (parenterally) as a result of its good water solubility and as a result of its low toxicity, in particular on account of a low hemolytic activity.

It is further an object of the present invention to make available a process for the preparation of a salt of the lipopeptide antibiotics of the asparagine type and in particular an improved process for the fermentative preparation of its acid precursors, in which lipopeptide antibiotics of the asparagine type are preferably produced.

Finally, it is an object of the present invention to make available a pharmaceutical which contains a salt of the lipopeptide antibiotics of the asparagine type having the desired advantageous properties.

It has now been found in the case of the lipopeptide antibiotics of the asparagine type that the various salts of the same lipopeptide (or the same corresponding acid) can have very different properties. For example, the sodium salts as a rule have a very good antibacterial activity and are readily soluble in water. However, these can only be kept for a limited period, in particular at elevated temperatures. Since in the case of medicaments and other commercial products stability is of great importance, e.g. for the handling of the goods, stable salt forms of the lipopeptide antibiotics are necessary.

Since the lipopeptide antibiotics of the asparagine type are amphoteric compounds having an isoelectric point in the acidic range, neutral salts can be prepared with numerous bases. Possible cations are monovalent and polyvalent ions, such as, for example, alkali metal, alkaline earth metal and other metal ions, but also salts with ammonia or with organic bases, such as amines. Examples of the latter are lysine and lysyllysine salts, which are very highly tolerable and have full activity.

Surprisingly, it has now been found that unlike the calcium salts of the lipopeptide antibiotics of the amphomycin type (in particular amphomycin), the calcium salts of the lipopeptide antibiotics of the asparagine type are not only active and tolerable, but also readily soluble in water and particularly stable, unlike the corresponding sodium salts.

Accordingly, the object set above is achieved by a calcium salt of the compound of the formula II

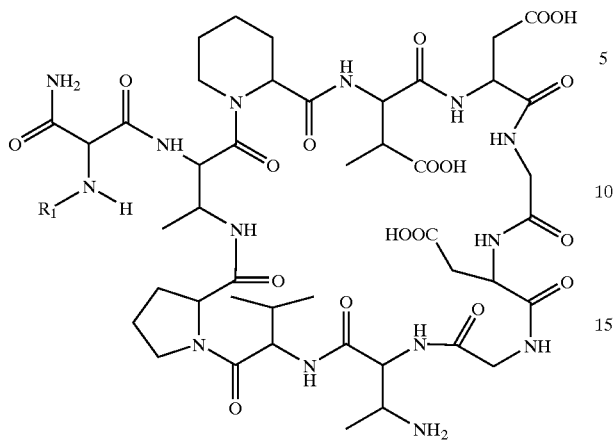

in which $R_1$ is a straight-chain or branched, saturated or unsaturated aliphatic acyl radical having 8 to 22 carbon atoms, which can optionally be interrupted by one or more phenyl or cycloalkyl groups or linked to such groups and can furthermore be optionally interrupted by oxygen.

Preferably, R1 in formula II is an acyl radical interrupted by a phenyl or cycloalkyl group or linked to such a group, for example

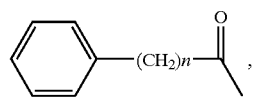   (1a)

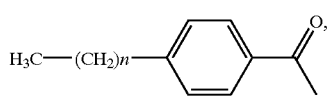   (1b)

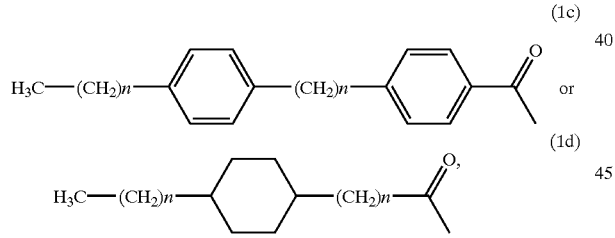

(1c)

(1d)

where n is an integer from 0 to 20.

Furthermore preferred is a calcium salt of the compound of the formula II which is distinguished in that R1 is an acyl radical interrupted by a phenyl or cycloalkyl group and by oxygen, preferably wherein R1 is

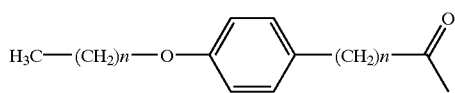   (2a)

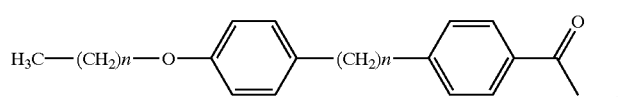

(2b)

where n is an integer from 0 to 20.

Particularly preferred is a calcium salt of the compound of the formula II which is distinguished in that R1 is a straight-chain or branched, saturated or unsaturated aliphatic acyl radical having 12 to 15 carbon atoms, where R1 in formula II preferably is a fatty acid radical of the formula shown below:

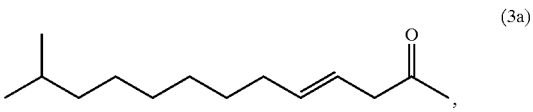   (3a)

   (3b)

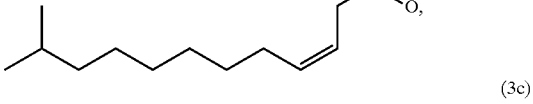   (3c)

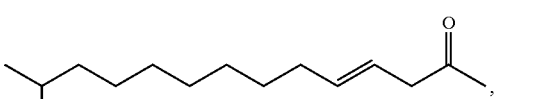   (3d)

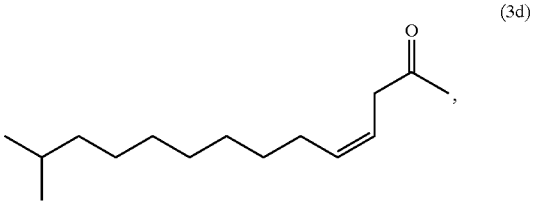

(3e)

(3f)

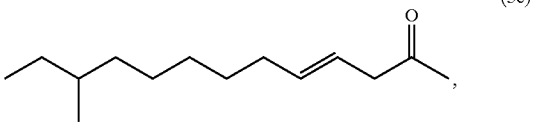

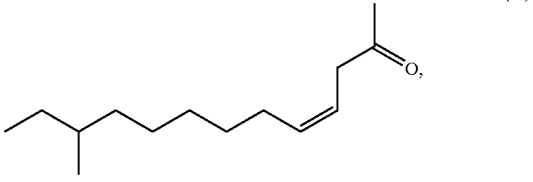

(3g)

or (3h)

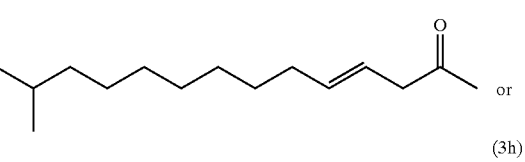

The calcium salt of the compound of the formula II can be present in two forms, as a dicalcium salt or as a monocalcium salt.

Depending on the number of anions and the fatty acid substituent (R1 in formula II), the dicalcium salt can be described in greater detail (i) for example in the case of a saturated fatty acid (R1 in formula II) by the empirical formula $$C_{46+n}H_{68+2n}N_{14}O_{19}Ca_2X_2, \quad \text{(ia)}$$

$$C_{46+n}H_{69+2n}N_{14}O_{19}Ca_2X_3 \text{ or} \quad \text{(ib)}$$

$$C_{46+n}H_{70+2n}N_{14}O_{19}Ca_2X_4, \quad \text{(ic)}$$

where in the empirical formula n is an integer from 7 to 21 and X is an anion, or (ii) for example in the case of a monounsaturated fatty acid (R1 in formula II) by the empirical formula $$C_{46+n}H_{66+2n}N_{14}O_{19}Ca_2X_2, \quad \text{(iia)}$$

$$C_{46+n}H_{67+2n}N_{14}O_{19}Ca_2X_3 \text{ or} \quad \text{(iib)}$$

$$C_{46+n}H_{68+2n}N_{14}O_{19}Ca_2X_4, \quad \text{(iic)}$$

where in the empirical formula n is an integer from 7 to 21 and X is an anion.

For example, the abovementioned, preferred calcium salts of the compound of the formula II(3c) and (3d) can be described in greater detail by the following empirical formulae if a dicalcium salt is present, where in the empirical formulae X is an anion:

$$C_{59}H_{92}N_{14}O_{19}Ca_2X_2, \quad \text{(3c, 3d/iia)}$$

$$C_{59}H_{93}N_{14}O_{19}Ca_2X_3 \text{ or} \quad \text{(3c, 3d/iib)}$$

$$C_{59}H_{94}N_{14}O_{19}Ca_2X_4. \quad \text{(3c, 3d/iic)}$$

Preferably, in all abovementioned empirical formulae, the anion X is a halide anion, Cl⁻, Br⁻ or I⁻, particularly preferably Cl⁻.

Depending on the fatty acid substituent (R1 in formula II), the monocalcium salt can furthermore be characterized in greater detail for example in the case of a saturated fatty acid (R1 in formula II) by the empirical formula $$C_{46+n}H_{68+2n}N_{14}O_{19}Ca \quad \text{(iii)}$$

or, for example, in the case of a monounsaturated fatty acid (R1 in formula II) by the empirical formula $$C_{46+n}H_{66+2n}N_{14}O_{19}Ca, \quad \text{(iv)}$$

where n in both empirical formulae is an integer from 7 to 21.

For example, the abovementioned, preferred calcium salts of the compound of the formula II (3c) and (3d) can be described in greater detail by the following empirical formula if a monocalcium salt is present:

$$C_{59}H_{92}N_{14}O_{19}Ca. \quad \text{(3c, 3d/iv)}$$

In the abovementioned, preferred calcium salts of the compound of the formula II (3c) and (3d), in contrast, the corresponding acid, namely the corresponding compound of the formula II, for example has the empirical formula $C_{59}H_{94}N_{14}O_{19}$.

The acid A1437-D mentioned below, corresponding to the abovementioned, preferred calcium salt (3d) (the corresponding compound of the formula II) has the structure shown below (FIG. 1):

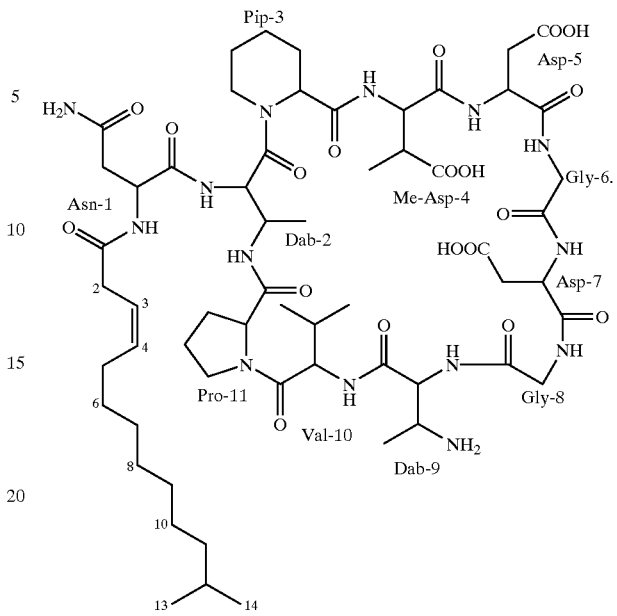

FIG. 1: Structural formula of A1437-D (acid form of 3d)

Table 1 lists the assignment of the ¹H and ¹³C-NMR signals as exemplified by the A1437-D sodium salt. The amino acid designations are abbreviated according to the international conventions, Dab=2,3-diaminobutyric acid, Me-Asp=β-methylaspartic acid, Pip=pipecolic acid, FA=fatty acid. The amino acids preferably have the following configuration: Pip-3: D; Me-Asp4: L-threo; Asp-5, -7: L; Dab-2: L-threo; Dab-9: D-erythro; Val-10: L; Pro-1 1: L; Asn-1: L.

TABLE 1

Chemical shifts of A 1437-D in CD₃CN/H₂O at 285 K[a)].

| AA | Proton/carbon | ¹H | ¹³C |
|---|---|---|---|
| Asn¹ | NH | 7.82 | — |
|  | α | 4.69 | 53.36 |
|  | β | 2.70/2.64 | 39.42 |
|  | C' | — | 174.59 |
|  | β-C' | — | 176.23 |
|  | NH₂ | 7.36/6.76 | — |
| Dab² | NH | 7.77 | — |
|  | α | 5.04 | 56.49 |
|  | β | 4.50 | 48.88 |
|  | γ | 1.05 | 20.76 |
|  | β-NH | 7.59 | — |
|  | C' | — | 172.56 |
| Pip³ | α | 4.64 | 57.39 |
|  | β | 2.23/1.68 | 28.86 |
|  | γ | 1.64/1.29 | 22.56 |
|  | δ | 1.76/1.70 | 26.30 |
|  | ε | 3.82/3.36 | 46.41 |
|  | C' | — | 175.34 |
| Me-Asp⁴ | NH | 8.93 | — |
|  | α | 4.56 | 58.07 |
|  | β | 2.51 | 50.6(broad) |
|  | γ | 1.05 | 17.24 |
|  | C' | — | 176.65 |
|  | β-C' | — | 184.13 |
| Asp⁵ | NH | 8.24 | — |
|  | α | 4.19 | 57.09 |
|  | β | 2.58/2.50 | 40.47 |
|  | C' | — | 177.34 |
|  | β-C' | — | 179.15 |

TABLE 1-continued

Chemical shifts of A 1437-D in $CD_3CN/H_2O$ at 285 K[a)].

| AA | Proton/carbon | $^1H$ | $^{13}C$ |
|---|---|---|---|
| Gly[6] | NH | 8.83 | — |
| | α | 4.23/3.67 | 45.32 |
| | C' | — | 174.48 |
| Asp[7] | NH | 7.68 | — |
| | α | 4.57 | 53.85 |
| | β | 3.18/2.44 | 41.93 |
| | C' | — | 176.17 |
| | β-C' | — | 179.21 |
| Gly[8] | NH | 8.10 | — |
| | α | 4.29/3.55 | 173.23 |
| | C' | — | 173.23 |
| Dab[9] | NH | 9.54(broad) | — |
| | α | 4.43 | 59.41 |
| | β | 3.54 | 53.45 |
| | γ | 1.34 | 19.78 |
| | C' | — | 172.45 |
| Val[10] | NH | 8.31 | — |
| | α | 4.02 | 62.58 |
| | β | 2.25 | 32.20 |
| | γ | 1.05 | 20.72 |
| | γ' | 0.94 | 21.39 |
| | C' | — | 175.42 |
| Pro[11] | α | 4.06 | 63.97 |
| | β | 2.20/1.74 | 32.50 |
| | γ | 1.99/1.91 | 27.91 |
| | δ | 3.83/3.55 | 50.93 |
| | C' | — | 173.57 |
| FA | 1 | — | 175.52 |
| | 2 | 3.03 | 36.84 |
| | 3 | 5.51 | 124.41 |
| | 4 | 5.61 | 136.65 |
| | 5 | 2.05 | 29.82 |
| | 6 | 1.35 | 32.40[b)] |
| | 7 | 1.25–1.35 | 32.14[b)] |
| | 8 | 1.25–1.35 | 31.97[b)] |
| | 9 | 1.25–1.35 | 31.83[b)] |
| | 10 | 1.29 | 29.96 |
| | 11 | 1.17 | 41.54 |
| | 12 | 1.53 | 30.51 |
| | 13,14 | 0.88 | 24.77 |

[a)]calibrated on sodium 2,2,3,3-$d_4$-3-(trimethylsilyl)propionate

It was then possible to observe that, for example, in the change from the A-1437-D sodium salt to the calcium salt (3d), the physicochemical properties of the antibiotic fundamentally change. Thus the specific rotation [α] of the sodium salt at the wavelength of the sodium D line and at 20° C. rises from +6 to over +52° if a soluble calcium salt, such as, for example, $CaCl_2$, is added to the aqueous solution. It seems reasonable to assume from this unreasonable behavior that the molecule undergoes a significant change in its conformation. This conformational change is also supported by the low conductivity of the A-1437-D calcium salt (3d/iv), which is markedly lower than would be expected for an ionic compound.

There are several possibilities for the preparation of calcium salts of the compound of the formula II. On the one hand, the restricted solubility of the calcium salts in selected solutions can be made usable. While the $Na^+$ or the $NH_4^+$ salts are very readily soluble in water or in methanol and are soluble in higher alcohols and other polar organic solvents, solubilities of the corresponding calcium salts in nonaqueous solvents are markedly reduced.

Accordingly, the process for the preparation of the calcium salt of the compound of the formula II described above is distinguished in that a sodium or ammonium salt of the compound of the formula II is dissolved in a suitable organic solvent, a calcium salt dissolved in ethanol is added to this solution and the calcium salt of the compound of the formula II is isolated as a precipitate. Preferably, the suitable organic solvent is ethanol. The calcium salt to be added dissolved in ethanol is preferably a calcium halide, $CaCl_2$, $CaBr_2$, $CaI_2$ or the corresponding hydrates. In this process, the dicalcium salts of the compound of the formula II preferably result.

For the preparation, for example, of the calcium salts (3d/iia) having the empirical formula $C_{59}H_{92}N_{14}O_{19}Ca_2X_2$, (3d/iib) having the empirical formula $C_{59}H_{93}N_{14}O_{19}Ca_2X_3$ or (3d/iic) having the empirical formula $C_{59}H_{94}N_{14}O_{19}Ca_2X_4$, a procedure can therefore be used in which the sodium or ammonium salt of A1437/D (the acid corresponding to (3d)) is dissolved in a suitable organic solvent, such as, for example, ethanol, and a calcium salt dissolved in ethanol is added to this solution. The A1437D calcium salt which is poorly soluble in the organic solvent is deposited here in the form of a precipitate. Calcium salts soluble in ethanol and suitable for the precipitation are, for example, $CaCl_2$, $CaBr_2$, $CaI_2$ and their hydrates. This precipitation process results in salts which, apart from the calcium cation, can additionally contain anions of the precipitation salt, for example the halides $Cl^-$, $Br^-$ and $I^-$. The empirical formulae of the precipitated calcium salts can, for example, read: $C_{59}H_{92}N_{14}O_{19}Ca_2halide_2$, such as, for example, $C_{59}H_{92}N_{14}O_{19}Ca_2Cl_2$ or $C_{59}H_{92}N_{14}O_{19}Ca_2I_2$ or $C_{59}H_{93}N_{14}O_{19}Ca_2halide_3$ such as, for example, $C_{59}H_{93}N_{14}O_{19}Ca_2Br_3$ or $C_{59}H_{93}N_{14}O_{19}Ca_2Cl_3$; depending on the precipitation conditions, however, other mixed salts can also be formed for which, inter alia, the composition $C_{59}H_{94}N_{14}O_{19}Ca_2halide_4$ is found. These mixed salts (A 1437 calcium mixed salts) are soluble in water and are therefore suitable for the treatment of bacterial infections or for preservation or alternatively for growth promotion in animal breeding, but they can also be used as intermediates for the preparation of other salts.

Crystallization is a further possibility of obtaining or of purifying calcium salts of the compound of the formula II. Here, the property of the antibiotic calcium salt of dissolving in pure water, in dimethyl sulfoxide, in pure methanol and in other polar solvents is used.

Accordingly, the process for the preparation of a calcium salt, preferably of the monocalcium salt, of the compound of the formula II is distinguished in that a dicalcium salt of the compound of the formula II, which, for example, can be obtained by the method described above, is dissolved in a polar solvent, then the solution obtained is treated with a less polar solvent or a mixture of less polar solvents and the calcium salt, preferably the monocalcium salt, is isolated as a precipitate.

A further process for the preparation of a calcium salt, preferably of the monocalcium salt, of the compound of the formula II is distinguished in that a sodium or ammonium salt of the compound of the formula II is dissolved in a polar solvent, a calcium salt dissolved in the same polar solvent is added to this solution, then the solution obtained is treated with a less polar solvent or a less polar solvent mixture and the calcium salt, preferably the monocalcium salt, is isolated as a precipitate.

Preferably, in the two process alternatives, the sodium or ammonium salt or the dicalcium salt of the compound of the formula II is dissolved in a polar solvent which is selected from the group consisting of water, dimethyl sulfoxide and methanol.

Preferably, the less polar solvent with which the solution obtained is treated is selected from the group consisting of alcohols, acetone and acetonitrile.

Preferably, the sodium or ammonium salt or the dicalcium salt of the compound of the formula II is dissolved in water, and the less polar solvent is methanol.

Advantageously, a mixture of methanol and butanol is added in both the process variants as a less polar solvent mixture.

Alternatively, the calcium salt, preferably the monocalcium salt, of the compound of the formula II can be prepared by dissolving a sodium or ammonium salt of the compound of the formula II in methanol, adding a calcium salt dissolved in the same solvent to this solution, then treating the solution obtained with water or a mixture of water and butanol and isolating the calcium salt, preferably the monocalcium salt, as a precipitate.

Preferably, in all these process variants the dissolved calcium salt preferably added is a calcium halide which is selected from the group consisting of $CaCl_2$, $CaBr_2$, $CaI_2$ and their hydrates.

For example, the A1437-D dicalcium salts can be dissolved in concentrated form in a highly dissolving solvent and then treated with an agent which is miscible but dissolves the antibiotic salt less. Examples of the latter are less polar, organic solvents, such as alcohols, acetone, acetonitrile and others. The mixture of water and methanol forms a special case. While these pure solvents readily dissolve A1437-D Ca salts, the mixtures of both solvents have distinctly poorer solvent properties. The A1437-D monocalcium salts (3d/iv) can thus be precipitated and crystallized from water (from methanol) with addition of methanol (water). In this way, calcium salts can be prepared or purified. The A1437-D monocalcium salt (3d/iv) readily forms gels in water-methanol mixtures. This gel formation is unfavorable for crystallization, since the crystallization rate is severely retarded thereby. For crystallization, measures must therefore be taken to suppress gel formation. Thus one measure can be, for example, the addition of small amounts of a suitable substance, such as, for example, butanol.

Another process for the preparation of the calcium salt of the compound of the formula II preferably of its monocalcium salt, for example the A1437-D monocalcium salt (3d/iv), consists in the use of a support, for example of adsorption resins, reverse-phase supports, molecular sieves and ion exchangers, which is loaded with an aqueous solution of a sodium or ammonium salt of the compound of the formula II (for example the sodium or ammonium salt of the compound A1437-D), which has been treated with a calcium halide, or alternatively with an aqueous solution of a dicalcium salt of the compound of the formula II (for example the dicalcium salts (3d/iia), (3d/iib) or (3d/iic)), after which the support is optionally washed with a suitable solvent and finally the calcium salt of the compound of the formula II, preferably the monocalcium salt, for example the A1437-D monocalcium salt (3d/iv), is eluted using a suitable solvent.

For use as adsorption resins, for example, Ambedite XAD 7 (Rohm & Haas), DIAION® HP20SS (Mitsubishi Chem. Corp.), Poros® 20 R2 or polyamide 6 (Riedel-deHaen) are suitable, when using reverse-phase supports, for example, LiChrosorb® RP-select B (E. Merck) is suitable. It is possible, however, also to employ supports which are usually used in hydrophobic interaction chromatography (HIC), for example for protein purification. Such supports are, for example, Phenyl Sepharose® or TSKgel Phenyl Toyopearl®. Moreover, molecular sieves such as are used for "size exclusion chromatography" or gel filtration chromatography are also suitable. The basis of this process is the tendency of the compound of the formula II (for example A1437-D) to bind calcium ions. When using the supports mentioned, a mixture of ammonium or sodium salts of the compound of the formula II with calcium salts is prepared in water and this mixture is separated on the supports in a manner known per se. Alternatively, it is also possible to apply an aqueous solution of an appropriate dicalcium salt. For example, an aqueous solution of A1437-D sodium salt and calcium chloride is applied to an adsorption resin, such as, for example, to DIAION HP® 20SS, the loaded resin is washed with water to remove excess salts, and then the calcium salt of the lipopeptide is eluted from the support using water-containing or anhydrous solvents, preferably using methanol. The A1437-calcium-containing fractions are dried. A product obtained in this way, for example, has the elemental composition $C_{59}H_{92}N_{14}O_{19}Ca$ (monocalcium salt of the compound of the formula II (3d/iv)).

For obtaining calcium salts of the compound of the formula II, it is furthermore possible to employ ion exchangers, preferably anion exchangers. In this method, for example, any desired aqueous, low-ion solution of the compound of the formula II is bound to an anion exchanger at pHs between pH 5 and pH 9, and after washing the loaded support with water the monocalcium salt of the compound of the formula II is eluted using a rising concentration of a calcium salt which is soluble in water. The column eluate, which contains the monocalcium salt, is desalted, for example by reverse osmosis, and dried. Alternatively, the monocalcium salt can be isolated by other processes, such as, for example, by crystallization.

The compounds of the formula II, the precursors of the calcium salts according to the invention, can be prepared advantageously, as disclosed in EP 0 629 636 A1, by fermentation of Actinoplanes sp., preferably *Actinoplanes friulensis* (DSM 7358), and alternatively, as described in EP 0 688 789 A1 (U.S. Pat. No. 5,629,288), derivatized by replacement of the acid radical R1 in formula II by an acid radical which does not occur naturally. The compounds of the formula II thus obtained can be reacted as described above to give their calcium salts.

The object set at the outset, to make available an improved process for the fermentative preparation of the compound of the formula II, the acid precursor of the calcium salts according to the invention, in which preferably the compound of the formula II is produced by the microorganism, is achieved in that in the fermentation of Actinoplanes spec., preferably of *Actinoplanes friulensis* DSM 7358, the fermentation solution is supplemented with one or more complexing agents, preferably chelating agents, and with the amino acid asparagine.

Preferably, the complexing agent used is citric acid or ethylenediamine tetraacetate (EDTA).

Advantageously, it is also possible to supplement the fermentation solution with EDTA and citric acid.

To increase the yield of a compound of the formula II in which R, for example, is a fatty acid radical of the formula (3a) or preferably (3b), the fermentation solution can additionally be supplemented with the amino acid L-leucine. To increase the yield of a compound of the formula II in which R1, for example, is a fatty acid radical of the formula (3c) or preferably (3d), the fermentation solution can additionally be supplemented with the amino acid L-valine.

Accordingly, the present invention also relates to a process for the preparation of a calcium salt of the compound of the formula II, which is distinguished in that in a first step the compound of the formula II, as described above, is prepared by fermentation of Actinoplanes spec., preferably *Actinoplanes friulensis* (DSM 7358), the fermentation solution being supplemented with one or more complexing agents, preferably chelating agents, and with the amino acid asparagine, and in a subsequent step the calcium salt of the compound of the formula II, as explained above, is obtained by precipitation, crystallization or treatment on a support.

The present invention also relates to a calcium salt of the compound of the formula II for use as a pharmaceutical.

The calcium salts of the compound of the formula II are preferably suitable for the production of a pharmaceutical against bacterial infections, the calcium salts (3c) and in particular (3d) or the dicalcium salts (3c/iia), (3c/iib) and (3c/iic) and in particular the dicalcium salts (3d/iia), (3d/iib) or (3d/iic) described above being particularly suitable, the dicalcium salt (3d/iia) being particularly preferred. The monocalcium salts of the compound of the formula II are particularly suitable for the preparation of a pharmaceutical against bacterial infections, the monocalcium salts (3c) and in particular (3d) having the empirical formula (3c, 3d/iv) $C_{59}H_{92}N_{14}O_{19}Ca$ being preferred. The abovementioned calcium salts of the compound of the formula II are preferably suitable for the production of a pharmaceutical against bacterial infections which are caused by Gram-positive bacteria, preferably by glycopeptide-resistant bacteria.

The pharmaceuticals comprising at least one calcium salt of the compound of the formula II can furthermore comprise the customary pharmaceutical auxiliaries.

For example, the dicalcium salt of the compound of the formula II, preferably the chloride 3d/iia, can be dissolved in water containing equal parts by weight of mannitol and then lyophilized for the production of a pharmaceutical.

The calcium salts of the compound of the formula II are particularly suitable on account of their solubility and their toxicological properties for parenteral administration in the form of an injectable solution. Accordingly, the present invention also relates to injectable solutions, comprising one or more calcium salts of the compound of the formula II, preferably the calcium salt (3d/iv) having the empirical formula $C_{59}H_{92}N_{14}O_{19}Ca$ or particularly preferably the calcium salt 3d/iia having the empirical formula $C_{59}H_{92}N_{14}O_{19}Ca_2Cl_2$.

For the production of an injection solution, the lyophilizate consisting of equal parts by weight of mannitol and calcium salt can be dissolved in suitably prepared water.

EXAMPLES

In the following examples, the acid form of the compounds of the formula I is called A1437. FIG. 2 gives an overview of the lipopeptides prepared or employed in the examples. The compounds of the formula I called A1437-A, -B and -G belong to the lipopeptides of the amphomycin type ($R^1$=OH in formula I), the compounds called A1437-C, -D and -H belong to the lipopeptides of the asparagine type ($R^1$=NH$_2$ in formula I) or are compounds of the formula II.

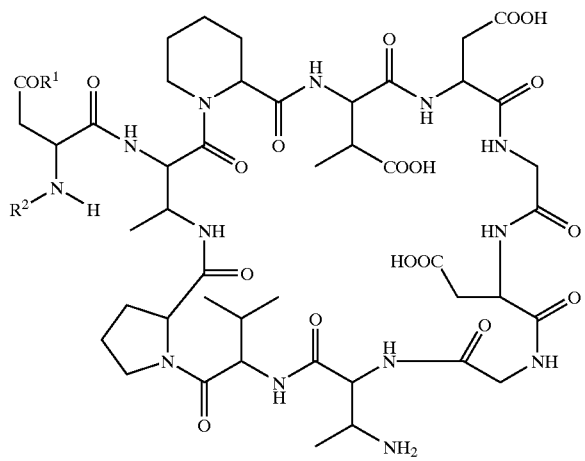

I

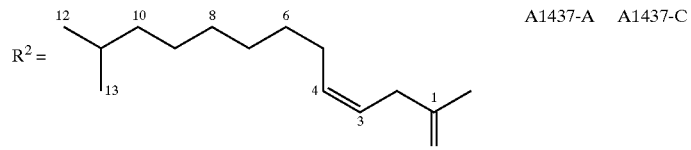

$R^1$ = OH   $R^1$ = NH$_2$

A1437-A   A1437-C

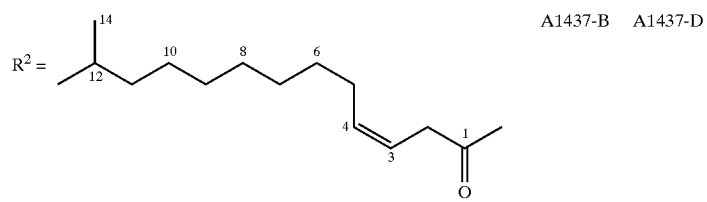

A1437-B   A1437-D

-continued

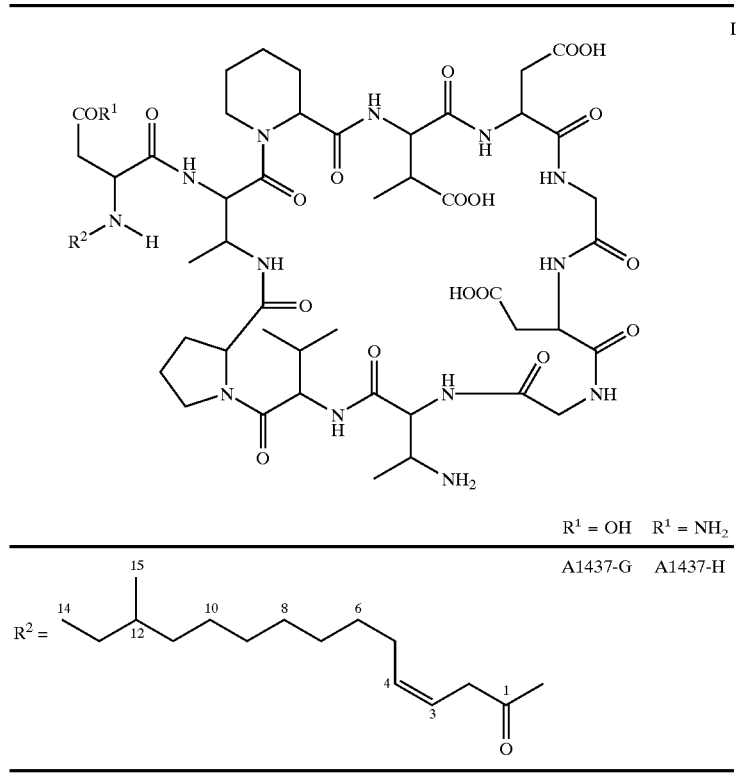

FIG. 2

As disclosed in EP 0 629 636, Actinoplanes spec., in particular *Actinoplanes friulensis* DSM 7358, forms by fermentation at least eight antibiotically active compounds of the formula I both of the amphomycin and of the asparagine type. As exemplified by the lipopeptides A1437-C and A1437-D (both compounds of the formula II), it is intended to show by which measures the yields of lipopeptides of the asparagine type can be significantly increased.

A1437-C and A1437-D are cyclic decapeptides having an exocyclic asparagine, which in the case of the C peptide is acylated with a C13-fatty acid and in the case of the D-peptide with a C14-fatty acid (FIG. 2). By feeding with the amino acids valine and leucine, which serve as starters for the synthesis of the respective fatty acid, the fermentation can be controlled in the direction of C- or D-peptide formation. However, at the same time as the C-peptide, a so-called A-peptide (A1437-A) is formed and at the same time as the D-peptide the B-peptide (A1437-B), which differs from C- or D-peptide only in the exocyclic position (aspartic acid instead of asparagine). As a rule, the titers of these peptides are even higher than those of the C- and D-peptide; in the most favorable case the ratio is about 1:1. Typically, the yields in the shaker culture varied between 40–150 mg/l of D-peptide with 50–250 mg/l of B-peptide (Example 1). In 30 l and 200 l steel fermenters it was typically possible to obtain 800–1100 mg/l of B-peptide with 20–40 mg/l of D-peptide (Example 2).

Possible causes of the reduced yields of A1437-D in fermenters are on the one hand possible adverse effects of metal ions, which pass into the culture solution due to abrasion of the fermenter, and the increased biomass formation, which leads to a relative lack of asparagine. In order to investigate these possibilities in greater detail, the culture solution was supplemented with EDTA (0.5 mM) and citric acid (10 mM) as ion scavengers and with asparagine (0.5 g/l). It was seen here that in the steel fermenter it was possible to achieve not only the shaker culture yield, but surprisingly also to significantly exceed it, and the D-peptide (A1437-D) became the prevalent component. The maximum yields were, for example, 1.2 g/l of A1437-D with 280 mg/l of A1437-B (Example 2). It was also possible to observe the selective shift and increase in the yield in the direction of A1437-D in the shaker culture. It was possible to increase the yield of A1437-D in shaker culture with the same average yield of A1437-B to, likewise, 1 g/l (Example 1).

Example 1

Increase in the yields of A1437-D with *Actinoplanes friulensis* DSM 7358 in shaker culture by addition of EDTA and asparagine.

A 300 ml Erlenmeyer flask with 100 ml of a nutrient solution (NL 1) of the following composition

| NL 1: | 30 g/l sucrose |  |
|---|---|---|
|  | 2 g/l KNO$_3$ |  |
|  | 1 g/l K$_2$HPO$_4$ |  |
|  | 0.5 g/l MgSO$_4$*7H$_2$O |  |
|  | 0.5 g/l KCl |  |
|  | 0.01 g/l FeSO$_4$*7H$_2$O |  |
|  | 2 g/l yeast extract |  |
|  | 5 g/l casein peptone | pH 7.3 | is inoculated with an ampoule (3 ml filling quantity) of mycelium which was stored at −190° C. in liquid nitrogen and is shaken for 5 days at 28° C. and 240 rpm.

A 2 l Erlenmeyer flask which is filled with 500 ml of the following nutrient solution (NL 2) is inoculated with 25 ml from this flask.

| NL 2: | 11 g/l sucrose |
| --- | --- |
| | 6 g/l Merck meat extract |
| | 0.3 g/l yeast extract |
| | 0.6 g/l MgSO$_4$*7H$_2$O |
| | 0.1 g/l KH$_2$PO$_4$ |
| | 3.9 g/l L-valine |
| | 0.0027 g/l FeCl$_3$*6H$_2$O    pH 71.2 |

The pH of the fermentation broth at the end of the fermentation is 7.0 to 7.8. The yields are typically between 20 and 155 mg/l of A1437-D with 60–250 mg/l of A1437-B.

| | Individual results | |
| --- | --- | --- |
| | A1437-B mg/l | A1437-D mg/l |
| Flask 1 | 140 | 85 |
| 2 | 180 | 140 |
| 3 | 240 | 155 |
| 4 | 110 | 130 |
| 5 | 90 | 20 |
| 6 | 60 | 40 |

By addition of 0.5 mM ethylenediaminotetraacetic acid (EDTA) and 0.5 g/l of asparagine, it was possible to increase the yields of A1437-D to about 1 g/l with the same average yield of A1437-B.

| | Individual results | |
| --- | --- | --- |
| | A1437-B mg/l | A1437-D mg/l |
| Flask 1 | 170 | 860 |
| 2 | 70 | 500 |
| 3 | 200 | 980 |
| 4 | 130 | 510 |
| 5 | 65 | 420 |
| 6 | 190 | 780 |

Example 2

Increase in the yields of A1437-D by fermentation of *Actinoplanes friulensis* DSM 7358 in 200 l fermenters by addition of EDTA and asparagine.

A 300 ml Erlenmeyer flask with 100 ml of the nutrient solution 1 is inoculated with the contents of an ampoule stored at −190° C. and shaken for 5 days at 28° C. and 240 rpm.

20 ml from this flask were transferred by inoculation to a 2 l Erlenmeyer flask filled with 500 ml of the same nutrient solution, which is shaken, likewise, for 5 days at 28° C. and 120 rpm.

The contents of 8 of these flasks are then transferred by inoculation to a 40 l fermenter which is filled with 30 l of the nutrient solution 2 and is driven at a stirrer speed of 0.8 m/sec. The pH of the fermentation broth at the end of the fermentation is 7.0 to 7.8.

The yields are typically between 20 and 40 mg/l of A1437-D at an A1437-B concentration of 800–1000 mg/l.

| | Individual results | |
| --- | --- | --- |
| | A1437-B mg/l | A1437-D mg/l |
| Fermenter 1 | 830 | 20 |
| 2 | 730 | 40 |
| 3 | 1050 | 40 |

By addition of 0.5 mM EDTA and 0.5 g/l of asparagine, it was possible to increase the A1437-D yields up to 1.2 g/l with considerable reduction of the A1437-B concentration.

| | Individual results | |
| --- | --- | --- |
| | A1437-B mg/l | A1437-D mg/l |
| Fermenter 1 | 220 | 690 |
| 2 | 140 | 930 |
| 3 | 430 | 1200 |

Example 3

Yields of A1437-C by fermentation of *Actinoplanes friulensis* DSM 7358 in shaker culture.

A 300 ml Erlenmeyer flask with 100 ml of the nutrient solution 1 is inoculated with the contents of an ampoule stored at −190° C. and shaken for 5 days at 28° C. and 240 rpm.

A 2 l Erlenmeyer flask which is filled with 500 ml of the following nutrient solution (NL 3) is inoculated with 25 ml from this flask.

| NL 3: | 11 g/l sucrose |
| --- | --- |
| | 6 g/l meat extract |
| | 0.3 g/l yeast extract |
| | 0.6 g/l MgSO$_4$*7H$_2$O |
| | 0.1 g/l KH$_2$PO$_4$ |
| | 3.9 g/l L-leucine |
| | 0.0027 g/l FeSO$_4$*7H$_2$O    pH 7.3 |

The pH of the fermentation broth at the end of the fermentation is 7.0 to 7.8. The yields are typically:

| | A1437-A mg/l | A1437-C mg/l |
| --- | --- | --- |
| Flask 1 | 166 | 298 |
| 2 | 543 | 168 |
| 3 | 518 | 173 |
| 4 | 435 | 210 |
| 5 | 345 | 230 |
| 6 | 225 | 215 |

Example 4

Table 2 shows a stability comparison of the A1437D sodium salt with the calcium mixed salt, $C_{59}H_{92}N_{14}O_{19}Ca_2I_2$, after storage at 40° C.

|  | Decomposition rate of the A1437 D, in % |
|---|---|
| A 1437-D sodium salt, | 3% |
| $C_{59}H_{92}N_{14}O_{19}Ca_2I_2$: | <0.5% |

Example 5

The antibacterial action of the A1437D Ca salt is summarized in Table 3. The value of the compound is based on its activity against the resistant and multiresistant disease pathogens: the spectrum of action makes the antibiotic—in addition to the good tolerability mentioned below—an enrichment of the pharmaceutical wealth.

Table 3: In-vitro activity of the A1437D Ca salt against Gram-positive bacteria in the serial dilution test indicated as the minimum inhibitory concentration (MIC)

| Bacterium | Resistance* | MIC values (µg/ml) |
|---|---|---|
| Staphyloc. aureus, 11HT3 | S | 0.04 |
| Staph. aureus, | ATCC 13709 | 0.6 |
| Staph. aureus, 11HT1 | novR | 0.15 |
| Staph. aureus, 11DU5 | novR, tetR | 0.08 |
| Staph. aureus, 11CB20 | oxaR, eryR, tetR | 0.6 |
| Staph. aureus, 11GO64 | oflR, oxaR, eryR, novR | 0.6 |
| Staphyloc. coagul. negativ | oflR, oxaR, tetR | 0.3 |
| Staph. epidermidis, GO20 | tetR | 0.3 |
| Staph. epidermidis, GO42 | oxaR | 0.3 |
| Streptoc. pyogenes, A1SJ1 | eryR | 0.6 |
| Streptoc. pyogenes, A1F16 | eryR | 0.6 |
| Streptoc. gr. G, GOCB2 | tetR, rifR, novR | 0.3 |
| Streptoc. pneumoniae 30B12 | eryR | 0.3 |
| Streptoc. milleri, GR12 | S | 0.3 |
| Streptoc. mitis, GR16 | eryR | 0.3 |
| Enteroc. faecium, AP9 | vanR, teiR | 0.6 |
| Enteroc. faecium, HT12 | teiR, vanR, eryR, tetR | 0.6 |
| Enteroc. faecium, IP2 | teiR, vanR, eryR, tetR | 0.6 |
| Enteroc. faecium, HM3 | teiR, vanR, eryR | 0.6 |
| Enteroc. gallinarium, HM8 | vanR, tetR | 0.15 |
| Enteroc. faecalis, HM9 | novR, vanR, eryR | 2.5 |
| Enteroc. faecalis, UC5 | ATCC 29212 novR | 2.5 |
| Enteroc. faecalis, DU18 | tetR, novR | 0.6 |

*S = sensitive, R = resistant, ery = erythromycin, nov = novobiocin, ofl = ofloxacin, oxa = oxacillin, rif = rifampicin, tei = teichoplanin, tet = tetracycline, van = vancomycin.

Example 6

Preparation of the A1437-D Dicalcium Iodide Salt ($C_{59}H_{92}N_{14}O_{19}Ca_2I_2$)

0.8 g of $CaI_2 \times 4H_2O$, dissolved in 3 ml of ethanol, is added slowly to a solution of 1.35 9 of A1437D sodium salt in 27 ml of absol. ethanol. A white, flocculent precipitate is gradually deposited here, which is collected after 30 minutes by centrifugation, washed three times with 10 ml each of cold ethyl alcohol and then dried in vacuo. 1.4 g of A1437D dicalcium iodide salt result. In addition to 79% of A1437D, which is determined by HPLC, the analyses give 5% Ca, 15.4% iodine and <0.2% sodium, corresponding to the composition $C_{59}H_{92}N_{14}O_{19}Ca_2I_2$.

Example 7

Preparation of the A1437D Calcium Bromide Salt 18 g of A1437D sodium salt are dissolved in 360 ml of absol. ethanol and treated at room temperature with 7 g of $CaBr_2$, dissolved in anhydrous ethanol. A white, flocculent precipitate is deposited here, which is collected by centrifuging at 8000 g for 15 minutes. Washing twice with 180 ml each of absol. ethanol and then drying in vacuo leads to 18.8 g of A1437D calcium bromide salt, whose analysis is 80% A1437D (HPLC, as the free acid), 6% calcium, 15% bromine and <0.1% sodium.

Example 8

Preparation of the A1437D-Monocalcium Salt by Solid-phase Extraction 1.1 g of A1437D calcium bromide salt prepared according to Example 7 are dissolved in water and applied to a prepared, 16 ml capacity column packed with MCl gel CHP20P, 75–150µ. Elution is carried out, as rapidly as possible, using a solvent gradient of 10% methanol in water (solution A) to 90% methanol and 10% butanol (solution B). First the impurities are washed from the column, then the A1437D monocalcium salt using pure solution B. Concentration in vacuo gives 0.8 g of A1437D monocalcium salt with 96% of A1437D (HPLC) and 3% calcium corresponding to the composition $C_{59}H_{92}N_{14}O_{19}Ca$.

Example 9

Reprecipitation of the A1437D Calcium Bromide Salt 1 g of A1437D calcium bromide salt, obtained as described in Example 7, is dissolved in 100 ml of water and treated with 36 ml of a mixture of methanol-butanol (9:1). The initially clear solution gradually becomes cloudy; it is allowed to stand for 12 hours for completion. The resulting precipitate is collected by centrifugation, washed with 50 ml of cold 40% strength methanol in water and dried in vacuo. 720 mg of monocalcium salt, $C_{59}H_{92}N_{14}O_{19}Ca$, are obtained with 3.1% of calcium, <1% of bromine and 95% of A1437D monocalcium salt.

Example 10

Obtainment of the A1437D Monocalcium Salt ($C_{59}H_{92}N_{14}O_{19}Ca$) by Methanol Precipitation 1 g of A1437D sodium salt are dissolved in 30 ml of water and treated with a solution of 200 mg of $CaCl_2$ in 10 ml of water. 14 ml of a mixture of 90% methanol and 10% butanol are added to the clear aqueous solution and after one hour the mixture is centrifuged at 4° C. The precipitate, which is washed twice with 30 ml each of aqueous methanol (40%), affords 810 mg of A1437D monocalcium salt with 3.2% calcium, <1% chloride and 94.5% A1437D monocalcium salt, calculated as the free acid.

Example 11

Determination of the In-vitro Hemolysis

For the measurement of hemolytic activity, freshly taken, venous human, Rhesus monkey or beagle dog blood is used. The blood is collected in heparinized tubes and distributed in aliquots of 200 µl into 12 polyethylene tubes. One aliquot is treated with 200 µl of distilled water and used as a 100% standard, another is mixed with 200 µl of physiological saline solution (0.9% NaCl). 200 µl each of substance dilutions in physiological saline solution to 1600, 800, 400, 200, 100, 50, 25, 12.5, 6.25 and 3.125 mg/l are distributed into the other tubes. All tubes are carefully swung and then incubated for 3 hours at 37° C. The 100% standard is then made up with 5 ml of distilled water, the other tubes with 5 ml each of physiological saline solution, and centrifuged at 700 g for 5 minutes.

The hemolysis is determined by measurement of the absorption of the supernatant in a spectrophotometer at a wavelength of 540 nm. The absorption of the standard with complete hemolysis is set at 100%. The absorption of the test preparation dilutions and of the 0% standard are measured and indicated as a percentage of the maximally inducible hemolysis. Table 4 shows the results of the hemolysis experiment with A1437-B, A1437-G in comparison with A1437-D Ca salt, carried out with monkey blood.

Table 4 shows by way of example the in vitro hemolysis of monkey blood as a function of the antibiotic concentrations.

TABLE 4

| | Antibiotic concentrations (mg/l): | | | | | | | |
|---|---|---|---|---|---|---|---|---|
| | 12.5 | 25 | 50 | 100 | 200 | 400 | 800 | 1600 |
| A1437-B | 0 | 2 | 7 | 11 | 16 | 25 | 31 | 39 |
| A1437-G | 0 | 5 | 8 | 12 | 17 | 25 | 30 | 40 |
| A1437-D Ca salt | 0 | 0 | 0 | 3 | 6 | 9 | 15 | 19 |

Example 12

Preparation of the A1437D Dicalcium Dichloride Salt From the Sodium Salt 15 g of A1437D sodium salt are completely dissolved in 400 ml of absolute ethanol and treated for 30 minutes with 2.52 [lacuna] of $CaCl_2$ (dry), dissolved in 100 ml of absolute ethanol, while stirring slowly and then allowed to stand at 0° C. for two hours. The precipitate is removed by centrifugation, washed with 200 ml of ethanol, removed again by centrifugation and dried in a high vacuum. The yield is 16.5 g. The final product contains 80.5% of A1437D lipopeptide, caculated as free acid, 4.5% of water, 5.1% of calcium, 7.5% of chloride and 2.1% of sodium corresponding to the empirical formula $C_{59}H_{92}N_{14}O_{19}Ca_2Cl_2$ with an impurity of about 4.6% of NaCl.

Example 13

Crystallization of the A1437D Dicalcium Dichloride Salt From the Sodium Salt 2.5 g of A1437D sodium salt, purity: 91.9%, are dissolved in 100 ml of water and treated with 10 g of $CaCl_2$ (e.g. Aldrich Cat. No.: 38,314-7). If in the course of this turbidity occurs, this is removed by filtration or by centrifugation. The crystallization is then slowly induced by addition of 35 ml of ethanol in the course of two hours, crystal formation gradually commencing at an organic solvent content of 15%. To accelerate the crystallization, the batch can be seeded at a solvent content of 20%. After addition of solvent is complete, the crystalline suspension is allowed to stand at room temperature for 24 hours, occasional stirring accelerating crystal formation. To complete the crystallization, the batch is cooled to +1° C. overnight and then suction-filtered. The crystallizate consisting of dense tufts of needles is washed with 5 ml of a cold mixture of 25% ethanol in water and then dried. 22 g of A1437D dicalcium dichloride salt, corresponding to 81% yield, are obtained in 97.9% purity. The mother liquor (5 g of organic solid, with approximately 63% purity) is allowed to stand with cooling, still further A1437D dicalcium dichloride salt crystallizing out in the course of several days.

Example 14

Preparation of an A1437D Dicalcium Dichloride Injection Solution 100 mg of A1437D dicalcium dichloride and 100 mg of apyrogenic mannitol are dissolved in 2 ml of sterile water and lyophilized. The entire lyophilizate, which is present as a powder, is dissolved in 2 ml of water for injection solutions, filled into a sterilized ampoule and the ampoule is sealed with a septum.

What is claimed is:
1. A calcium salt of the compound of the formula II

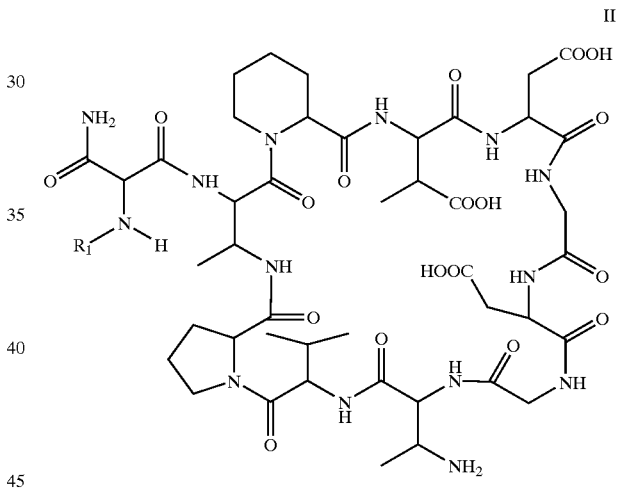

in which $R_1$ is a straight-chain or branched, saturated or unsaturated aliphatic acyl radical having 8 to 22 carbon atoms, which can optionally be interrupted by one or more phenyl or cycloalkyl groups or linked to such groups and can furthermore optionally be interrupted by oxygen.

2. A calcium salt as claimed in claim 1, wherein R1 is an acyl radical interrupted by a phenyl or cycloalkyl group or linked to such a group.

3. A calcium salt as claimed in claim 2, wherein R1 is

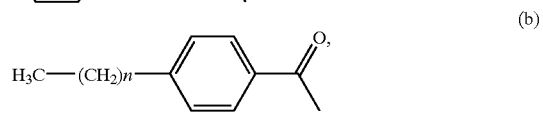

-continued

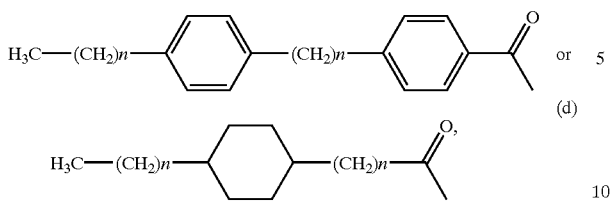

where n is an integer from 0 to 20.

4. A calcium salt as claimed in claim 1, wherein R1 is an acyl radical interrupted by a phenyl or cycloalkyl group and by oxygen.

5. A calcium salt as claimed in claim 4, wherein R1 is

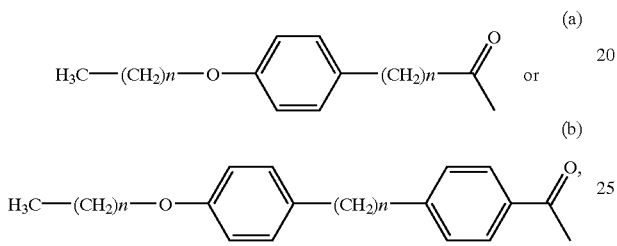

where n is an integer from 0 to 20.

6. A calcium salt as claimed in claim 1, wherein R1 is a straight-chain or branched, saturated or unsaturated aliphatic acyl radical having 12 to 15 carbon atoms.

7. A calcium salt as claimed in claim 6, wherein R1 is

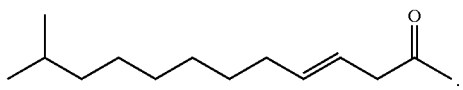

8. A calcium salt as claimed in claim 6, wherein R1 is

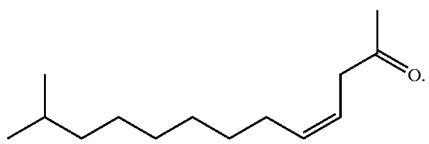

9. A calcium salt as claimed in claim 6, wherein R1 is

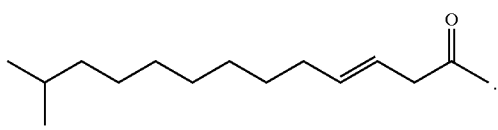

10. A calcium salt as claimed in claim 6, wherein R1 is

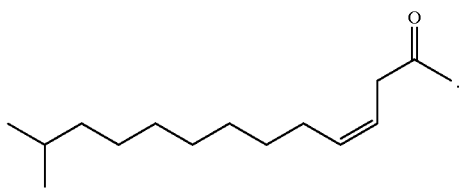

11. A calcium salt as claimed in claim 6, wherein R1 is

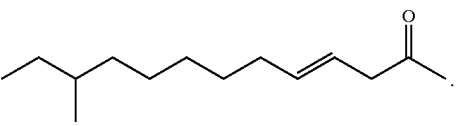

12. A calcium salt as claimed in claim 6, wherein R1 is

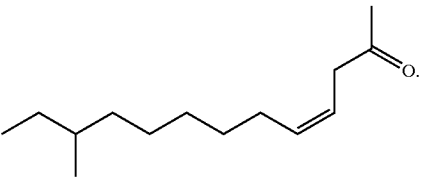

13. A calcium salt as claimed in claim 6, wherein R1 is

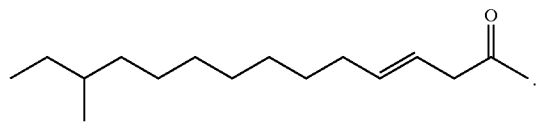

14. A calcium salt as claimed in claim 6, wherein R1 is

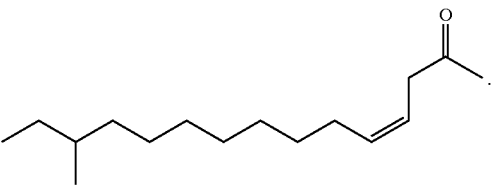

15. A calcium salt according to claim 1, which furthermore has the empirical formula $C_{46+n}H_{68+2n}N_{14}O_{19}Ca_2X_2$, in which n is an integer from 7 to 21 and X is an anion.

16. A calcium salt according to claim 1, which furthermore has the empirical formula $C_{46+n}H_{69+2n}N_{14}O_{19}Ca_2X_3$, in which n is an integer from 7 to 21 and X is an anion.

17. A calcium salt according to claim 1, which furthermore has the empirical formula $C_{46+n}H_{70+2n}N_{14}O_{19}Ca_2X_4$, in which n is an integer from 7 to 21 and X is an anion.

18. A calcium salt as claimed in claim 1, which furthermore has the empirical formula $C_{46+n}H_{66+2n}N_{14}O_{19}Ca_2X_2$, in which n is an integer from 7 to 21 and X is an anion.

19. A calcium salt as claimed in claims 1, which furthermore has the empirical formula $C_{46+n}H_{67+2n}N_{14}O_{19}Ca_2X_3$, in which n is an integer from 7 to 21 and X is an anion.

20. A calcium salt as claimed in claim 1, which furthermore has the empirical formula $C_{46+n}H_{68+2n}N_{14}O_{19}Ca_2X_4$, in which n is an integer from 7 to 21 and X is an anion.

21. A calcium salt as claimed in claim 10, which furthermore has the empirical formula $C_{59}H_{92}N_{14}O_{19}Ca_2X_2$, in which X is an anion.

22. A calcium salt as claimed in claim 10, which furthermore has the empirical formula $C_{59}H_{93}N_{14}O_{19}Ca_2X_3$, in which X is an anion.

23. A calcium salt as claimed in claim 10, which furthermore has the empirical formula $C_{59}H_{94}N_{14}O_{19}Ca_2X_4$, in which X is an anion.

24. A calcium salt as claimed in claim 18, wherein X is a halide anion.

25. A calcium salt as claimed in claim 24, wherein X is $Cl^-$.

26. A calcium salt as claimed in claim 1, which furthermore has the empirical formula $C_{46+n}H_{68+2n}N_{14}O_{19}Ca$, in which n is an integer from 7 to 21.

27. A calcium salt as claimed in claim 1, which furthermore has the empirical formula $C_{46+n}H_{66+2n}N_{14}O_{19}Ca$, in which n is an integer from 7 to 21.

28. A calcium salt as claimed in claim 10, which furthermore has the empirical formula $C_{59}H_{92}N_{14}O_{19}Ca$.

29. A process for the preparation of a calcium salt as claimed in claim 1, which comprises dissolving a sodium or ammonium salt of the compound of the formula II

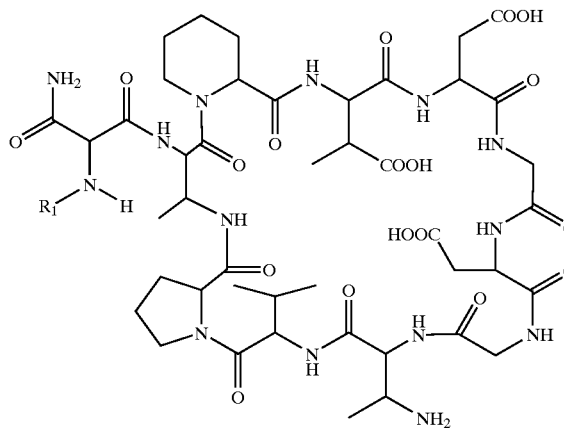

in which R1 is a straight-chain or branched, saturated or unsaturated aliphatic acyl radical having 8 to 22 carbon atoms, which can optionall be interrupted by one or more phenyl or cycloalkyl groups or linked to such groups and can furthermore optionally be interrupted by oxygen,
   in a suitable organic solvent, adding a calcium salt dissolved in ethanol to this solution and isolating the calcium salt as claimed in claim 1 as a precipitate.

30. The process as claimed in claim 29, wherein the suitable organic solvent is ethanol.

31. The process as claimed in claim 29, wherein a calcium halide dissolved in ethanol, which is selected from the group consisting of $CaCl_2$, $CaBr_2$, $CaI_2$ and their hydrates, is added.

32. A process for the preparation of a calcium salt as claimed in claim 27, which comprises dissolving a calcium salt of the compound of formula II

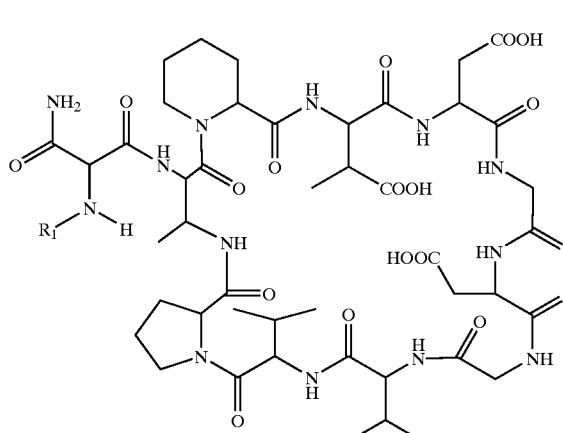

in which R1 is a straight-chain or branched, saturated or unsaturated aliphatic acyl radical having 8 to 22 carbon atoms which can optionally be interrupted by one or more phenyl or cycloalkyl groups or linked to such groups and can furthermore optionally be interrupted by oxygen, which furthermore has the empirical formula $C_{46+n}H_{66+2n}N_{14}O_9Ca_2X_2$, in which n is an integer from 7 to 21 and X is an anion, in a polar solvent, then treating the solution obtained with a less polar solvent or a mixture of less polar solvents and isolating the calcium salt as claimed in claim 27 as a precipitate.

33. A process for the preparation of a calcium salt as claimed in claim 1, which comprises dissolving a sodium or ammonium salt of the compound of the formula II

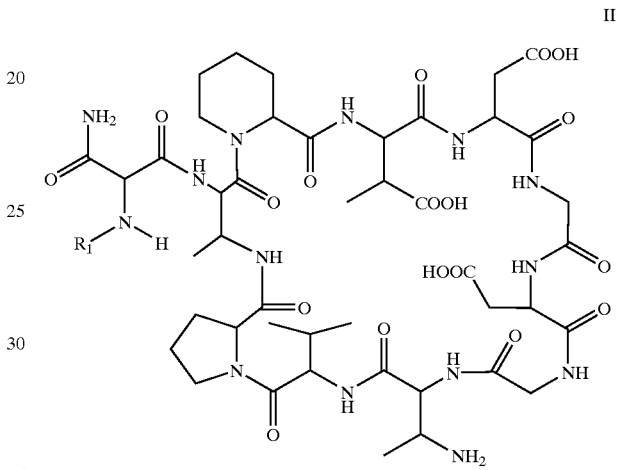

in which R1 is a straight-chain or branched, saturated or unsaturated aliphatic acyl radical having 8 to 22 carbon atoms, which can optionally be interrupted by one or more phenyl or cycloalkyl groups or linked to such groups and can furthermore optionally be interrupted by oxygen,
   in a polar solvent, adding a calcium salt dissolved in the same solvent to this solution, then treating the solution obtained with a less polar solvent or a less polar solvent mixture and isolating the calcium salt as claimed in claim 1 as a precipitate.

34. The process as claimed in claim 32 or 33, wherein the sodium or ammonium salt of the compound of the formula II or the calcium salt of the compound of formula II is dissolved in polar solvent which is selected from the group consisting of water dimethyl sulfoxide and methanol.

35. The process as claimed in claim 32 or 33, wherein the less polar solvent is selected from the group consisting of alcohols, acetone and acetonitrile.

36. The process as claimed in claim 32 or 33, wherein the sodium or ammonium salt of the compound of the formula II or the calcium salt of the compound of formula II is dissolved in water and the less polar solvent is methanol.

37. The process as claimed in claim 36, wherein, as a less polar solvent mixture, a mixture of methanol and butanol is added.

38. A process for the preparation of a calcium salt as claimed in claim 1, which comprises dissolving a sodium or ammonium salt of the compound of the formula II

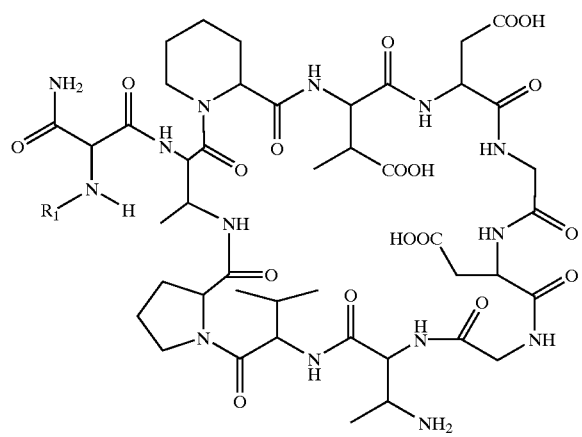

in which R1 is a straight-chain or branched, saturated or unsaturated aliphatic acyl radical having 8 to 22 carbon atoms, which can optionally be interrupted by one or more phenyl or cycloalkyl groups or linked to such groups and can furthermore optionally be interrupted by oxygen, in methanol, adding a calcium salt dissolved in the same solvent to this solution, then treating the solution obtained with water or a mixture of water and butanol and isolating the calcium salt as claimed in claim 1 as a precipitate.

39. The process as claimed in one or more of claim 33, wherein, as a dissolved calcium salt, a calcium halide which is selected from the group consisting of $CaCl_2$, $CaBr_2$, $CaI_2$ and their hydrates is added.

40. A process for the preparation of a calcium salt as claimed in claim 27, which comprises treating an aqueous solution of a sodium or ammonium salt of the compound of the formula II

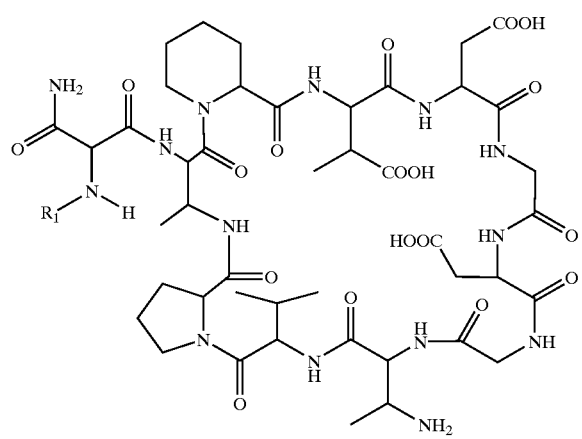

in which R1 is a straight-chain or branched, saturated or unsaturated aliphatic acyl radical having 8 to 22 carbon atoms, which can optionally be interrupted by one or more phenyl or cycloalkyl groups or linked to such groups and can furthermore optionally be interrupted by oxygen, with a calcium halide and applying this solution or alternatively an aqueous solution of a calcium salt of the compound of formula II in which R1 is a straight-chain or branched, saturated or unsaturated aliphatic acyl radical having 8 to 22 carbon atoms, which can optionally be interrupted by one or more phenyl or cycloalkyl groups or linked to such groups and can furthermore optionally be interrupted by oxygen, which furthermore has the empirical formula $C_{46+n}H_{66+2n}N_{14}O_{19}Ca_2X_2$, in which n is an integer from 7 to 21 and X is an anion, to a support which is selected from the group consisting of the adsorption resins, the reverse-phase supports, molecular sieves and the ion exchangers, and finally eluting the calcium salt as calcium in claim 27 using a suitable eluent.

41. A process for the preparation of a calcium salt of the compound of formula II as claimed in claim 1

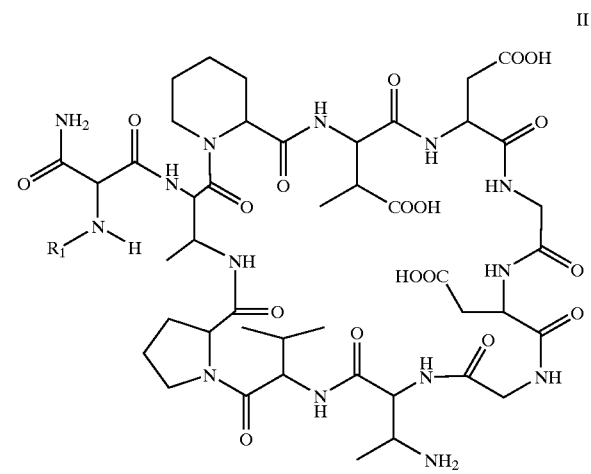

in which $R_1$ is a straight-chain or branched, saturated or unsaturated aliphatic acyl radical having 8 to 22 carbon atoms, which can optionally be interrupted by one or more phenyl or cycloalkyl groups or linked to such groups and can furthermore optionally be interrupted by oxygen, which comprises fermenting Actinoplanes spec., and supplementing the fermentation solution with one or more complexing agents and with asparagine.

42. The process as claimed in claim 41, wherein the complexing agent is citric acid.

43. The process as claimed in claim 41, wherein the complexing agent is EDTA.

44. The process as claimed in claim 41, wherein the fermentation solution is supplemented with EDTA and citric acid as complexing agents.

45. The process as claimed in claim 41, wherein in the compound of formula II R1 is

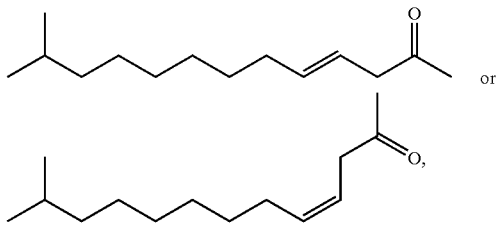

and wherein the fermentation solution is further supplemented with L-leucine.

46. The process as claimed in claim 41, wherein in the compound of formula II R1 is

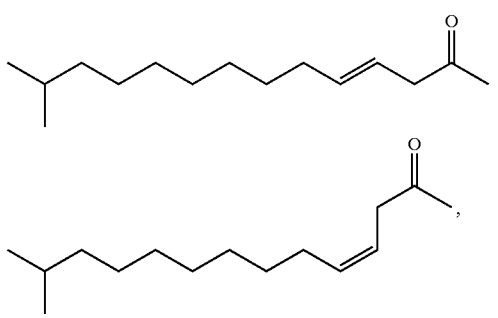

and wherein the fermentation solution is further supplemented with L-valine.

47. The process as claimed in claim 41, wherein *Actinoplanes friulensis* DSM 7358 is fermented.

48. A process for the preparation of a calcium salt as claimed in claim 1, which comprises first preparing a compound of the formula II

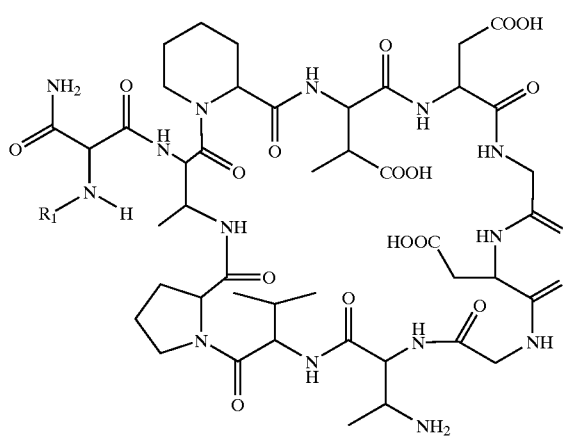

in which R1 is a straight-chain or branched, saturated or unsaturated aliphatic acyl radical having 8 to 22 carbon atoms which can optionally be interrupted by one or more phenyl or cycloalkyl groups or linked to such groups and can furthermore optionally be interrupted by oxygen, by fermenting Actinoplanes spec., and supplementing the fermentation solution with one or more complexing agents and with asparagines, converting the compound of the formula II into the sodium or ammonium salt, dissolving the sodium or ammonium salt in a suitable organic solvent, adding a calcium salt dissolved in ethanol to this solution and isolating the calcium salt as claimed in claim 1.

49. A pharmaceutical composition comprising one or more calcium salts as claimed in claim 1 and a pharmaceutical auxiliary.

50. A pharmaceutical composition comprising at least one calcium salt as claimed in claim 25 and a pharmaceutical auxiliary.

51. A pharmaceutical composition comprising at least one calcium salt as claimed in claim 28 and a pharmaceutical auxiliary.

52. An injectable solution comprising one or more calcium salts as claimed in claim 1.

53. An injectable solution comprising at least one calcium salt as claimed in claim 25.

54. An injectable solution comprising at least one calcium salt as claimed in claim 28.

55. A method for the treatment of a bacterial infection, which comprises administering to a host in need of the treatment an effective amount of a calcium salt as claimed in claim 1.

56. A method as claimed in claim 55, wherein the bacterial infection is caused by Gram-positive bacteria.

57. A method as claimed in claim 56, wherein the Gram-positive bacteria are glycopeptide-resistant bacteria.

58. A method for the treatment of a bacterial infection, which comprises administering to a host in need of the treatment an effective amount of a calcium salt as claimed in claim 25.

59. A method as claimed in claim 58, wherein the bacterial infection is caused by Gram-positive bacteria.

60. A method as claimed in claim 59, wherein the Gram-positive bacteria are glycopeptide-resistant bacteria.

61. A method for the treatment of a bacterial infection, which comprises administering to a host in need of the treatment an effective amount of a calcium salt as claimed in claim 28.

62. A method as claimed in claim 61, wherein the bacterial infection is caused by Gram-positive bacteria.

63. A method as claimed in claim 62, wherein the Gram-positive bacteria are glycopeptide-resistant bacteria.

* * * * *

UNITED STATES PATENT AND TRADEMARK OFFICE
CERTIFICATE OF CORRECTION

PATENT NO. : 6,624,143 B1  Page 1 of 1
DATED : September 23, 2003
INVENTOR(S) : Vertesy et al.

It is certified that error appears in the above-identified patent and that said Letters Patent is hereby corrected as shown below:

Column 22,
Line 49, "claims 1," should read -- claim 1, --.

Column 23,
Line 33, "optionall" should read -- optionally --.

Column 24,
Line 3, after "atoms", insert a comma.
Line 8, "$H_{66+2n}N_{14}O_9Ca_2X_2$," should read -- $H_{66+2n}N_{14}O_{19}Ca_2X_2$, --.
Line 52, after "dissolved in" and before "polar solvent", insert -- a --.

Column 25,
Line 31, after "as claimed in", delete "one or more of".

Column 26,
Line 61, "fermenting Actinoplanes spec.," should read -- fermenting a species of *Actinoplanes*, --.

Column 28,
Line 3, after "atoms", insert a comma.
Line 8, "fermenting Actinoplanes spec.," should read -- fermenting a species of *Actinoplanes*, --.

Signed and Sealed this

Ninth Day of December, 2003

JAMES E. ROGAN
*Director of the United States Patent and Trademark Office*